United States Patent
Toyama et al.

(10) Patent No.: US 9,475,315 B2
(45) Date of Patent: Oct. 25, 2016

(54) LIQUID DISCHARGE APPARATUS

(71) Applicant: SEIKO EPSON CORPORATION, Tokyo (JP)

(72) Inventors: Hiroshi Toyama, Nagano (JP); Tomoyuki Shiiya, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/017,958

(22) Filed: Feb. 8, 2016

(65) Prior Publication Data

US 2016/0236475 A1 Aug. 18, 2016

(30) Foreign Application Priority Data

Feb. 18, 2015 (JP) ................. 2015-029489

(51) Int. Cl.
| | |
|---|---|
| *B41J 29/393* | (2006.01) |
| *B41J 15/00* | (2006.01) |
| *B41J 25/308* | (2006.01) |
| *B41J 25/312* | (2006.01) |
| *B41J 25/316* | (2006.01) |
| *B41J 2/045* | (2006.01) |
| *B41J 2/165* | (2006.01) |
| *B41J 11/00* | (2006.01) |
| *B41J 11/20* | (2006.01) |
| *B41J 11/24* | (2006.01) |
| *B41J 13/00* | (2006.01) |
| *B41J 13/02* | (2006.01) |
| *B41J 13/036* | (2006.01) |

(52) U.S. Cl.
CPC ............ *B41J 15/00* (2013.01); *B41J 2/04556* (2013.01); *B41J 2/165* (2013.01); *B41J 11/005* (2013.01); *B41J 11/0095* (2013.01); *B41J 11/20* (2013.01); *B41J 11/24* (2013.01); *B41J 13/0027* (2013.01); *B41J 13/0063* (2013.01); *B41J 13/02* (2013.01); *B41J 13/025* (2013.01); *B41J 13/036* (2013.01); *B41J 25/308* (2013.01); *B41J 25/3084* (2013.01); *B41J 25/3088* (2013.01); *B41J 25/312* (2013.01); *B41J 25/316* (2013.01)

(58) Field of Classification Search
CPC ...... B41J 15/00; B41J 13/036; B41J 13/025; B41J 11/24; B41J 13/0027; B41J 13/02; B41J 11/20; B41J 13/0063; B41J 2/04556; B41J 11/005; B41J 11/0095; B41J 2/165; B41J 25/308; B41J 25/3088; B41J 25/3084; B41J 25/316; B41J 25/312
See application file for complete search history.

(56) References Cited

U.S. PATENT DOCUMENTS

| | | | | |
|---|---|---|---|---|
| 5,204,726 A | * | 4/1993 | Choi | ..................... B65H 7/06 271/259 |
| 2002/0197083 A1 | * | 12/2002 | Yoshino | .............. G03G 15/101 399/237 |

FOREIGN PATENT DOCUMENTS

| | | | |
|---|---|---|---|
| JP | 2001-262459 A | 9/2001 | |
| JP | 2001262459 | * 9/2001 | ............ B41J 2/185 |
| JP | 2005-199507 A | 7/2005 | |
| JP | 2012-071962 A | 4/2012 | |

* cited by examiner

*Primary Examiner* — Julian Huffman
(74) *Attorney, Agent, or Firm* — Global IP Counselors, LLP

(57) ABSTRACT

The liquid discharge apparatus includes a support member supporting a medium while rotating, a head facing the support member and discharging a liquid, a conveyance part conveying a medium between the support member and the head, and a foreign matter detection unit detecting a foreign matter heading toward between the support member and the head in association with the conveyance of the medium. The foreign matter detection unit has a movable roller that faces the support member upstream relative to the head in a conveyance direction of the medium, and nips the medium between the support member and the movable roller, a rotational support member rotatably supporting the movable roller to allow inclination of the movable roller relative to a rotational axis direction, which is a center of rotation of the support member, and a retention member movably retaining the rotational support member in a direction toward the support member.

9 Claims, 3 Drawing Sheets

LIQUID DISCHARGE APPARATUS

CROSS-REFERENCE TO RELATED APPLICATIONS

This application claims priority to Japanese Patent Application No. 2015-029489 filed on Feb. 18, 2015. The entire disclosure of Japanese Patent Application No. 2015-029489 is hereby incorporated herein by reference.

BACKGROUND

1. Technical Field

The present invention relates to a technique for detecting a foreign matter present on a medium in a liquid discharge apparatus for discharging a liquid from a head onto a medium supported by a support member.

2. Related Art

There is a known printing apparatus provided with a support member for supporting a medium and a head that faces the support member, printing being performed onto the medium by the discharging of ink from the head onto the medium supported on the support member. Such a printing apparatus executes printing onto the medium while also conveying the medium between the support member and the head. At this time, if a foreign matter is present on the medium, the foreign matter may end up coming into contact with the head and damaging the head. In light of such circumstances, techniques for detecting a foreign matter present on a medium have long been proposed.

For example, a foreign matter detection apparatus of Japanese laid-open patent publication No. 2012-71962 is provided with a conveyance roller for conveying a continuous document, and a movable roller that faces the conveyance roller, the continuous document being nipped between the movable roller and the conveyance roller. The movable roller can be displaced in a direction of approach towards or withdrawal from the conveyance roller; if a foreign matter present on the continuous document passes between the movable roller and the conveyance roller, the movable roller is pressed and displaced by the foreign matter. As such, the foreign matter can be detected on the basis of the displacement of the movable roller.

In a configuration for thus detecting a foreign matter on a medium on the basis of displacement of a movable roller nipping the medium with a support member on the other side, it becomes more difficult to detect the foreign matter on the medium if there is a vacant clearance between the medium and the movable roller. However, there are instances where, for example, the surface of the support member ends up being inclined due to causes such as thermal deformation, creating a vacant clearance between the movable roller and the medium supported by the support member, and lowering the accuracy of detection of a foreign matter present on the medium.

SUMMARY

Having been made in light of the problem described above, the present invention addresses the problem of providing a technique for curbing the formation of a clearance between a movable roller and a medium supported by a support member, and making it possible to improve the accuracy of detection of a foreign matter present on the medium.

In order to solve the problem described above, a liquid discharge apparatus according to an aspect of the present invention includes a support member configured to support a medium while rotating, a head facing the support member and configured to discharge a liquid onto the medium supported by the support member, a conveyance part configured to convey the medium between the support member and the head, and a foreign matter detection unit configured to detect a foreign matter heading toward between the support member and the head, in association with a conveyance of the medium by the conveyance part. The foreign matter detection unit has a movable roller that faces the support member on an upstream side of the head in a direction of conveyance of the medium being conveyed by the conveyance part, and is configured to nip the medium between the support member and the movable roller, a rotational support member rotatably supporting the movable roller so as to allow inclination of the movable roller relative to a rotational axis direction, which is a center of rotation of the support member, and a retention member movably retaining the rotational support member in a direction going toward the support member.

With the aspect of the invention (liquid discharge apparatus) configured in this manner, the medium is supported by the rotatable support member, and the medium is nipped between the movable roller and the support member. With such a configuration, the support member and the movable roller are each rotatable in association with the conveyance of the medium. The rotational support member that rotatably supports the movable roller is retained by the retention member in a state allowing for movement in the direction toward the support member, i.e., the movable roller can move in the direction toward the support member. As such, when a foreign matter present on the medium passes between the movable roller and the support member, the movable roller is displaced by being pushed by the foreign matter.

In particular, in the aspect of the invention, the movable roller is rotatably supported by the rotational support member in a state of being inclinable relative to the rotational axis direction, which is the center of rotation of the support member. As such, in a case such as where the surface of the support member has become deformed, the movable roller can be inclined in conformity with such deformation. As such, it becomes possible to curb the formation of a clearance between the movable roller and the medium supported by the support member, and to improve the accuracy of detection of a foreign matter present on the medium.

The liquid discharge apparatus may be configured such that the foreign matter detection unit has an urging member configured to urge the retention member toward the support member. With such a configuration, the urging force of the urging member makes it possible for the movable roller, which is inclined in conformity with the deformation of the surface of the support member, to be pressed toward the support member. As a result, any clearance between the movable roller and the medium supported by the support member can be more reliably curbed.

A variety of configurations can be considered for the specific configuration of the rotational support member rotationally supporting the movable roller so as to be inclinable relative to the rotational axis direction, which is the center of rotation of the support member. Therefore, the rotational support member may be a spherical plain bearing, or the movable roller may be supported by a resin.

The liquid discharge apparatus may be configured such that the support member is a rotating drum.

The liquid discharge apparatus may be configured such that a hardness of a peripheral surface where the movable roller is in contact with the medium is 80 degrees or more. With such a configuration, it is possible to curb deformation of the peripheral surface of the movable roller associated with contact with a foreign matter. As a result, the movable roller can be precisely displaced in association with the passing of a foreign matter between the movable roller and the support member.

The liquid discharge apparatus may be configured such that the foreign matter detection unit has a sensor configured to detect displacement of the movable roller relative to the support member. With such a configuration, a foreign matter present on the medium can be detected on the basis of the output of the sensor.

Then, the liquid discharge apparatus may be configured such that the sensor is configured to detect the displacement of the movable roller on the basis of displacement of the retention member. A foreign matter present on the medium can still be detected with such a configuration.

It is particularly suitable to apply the aspect of the invention to a liquid discharge apparatus which further includes a light irradiation part configured to irradiate the liquid discharged onto the medium from the head with light, and with which the liquid is cured while being heated when irradiated with the light from the light irradiation part. Namely, with such a liquid discharge apparatus, the heating of the liquid is likely to cause the support member to undergo thermal deformation. Therefore, applying the aspect of the invention makes it possible to curb any clearance between the movable roller and the medium supported by the support member, even in spite of thermal deformation of the support member, and possible to improve the accuracy of detection of a foreign matter present on the medium.

BRIEF DESCRIPTION OF THE DRAWINGS

Referring now to the attached drawings which form a part of this original disclosure.

DETAILED DESCRIPTION OF EXEMPLARY EMBODIMENTS

Figure 1:
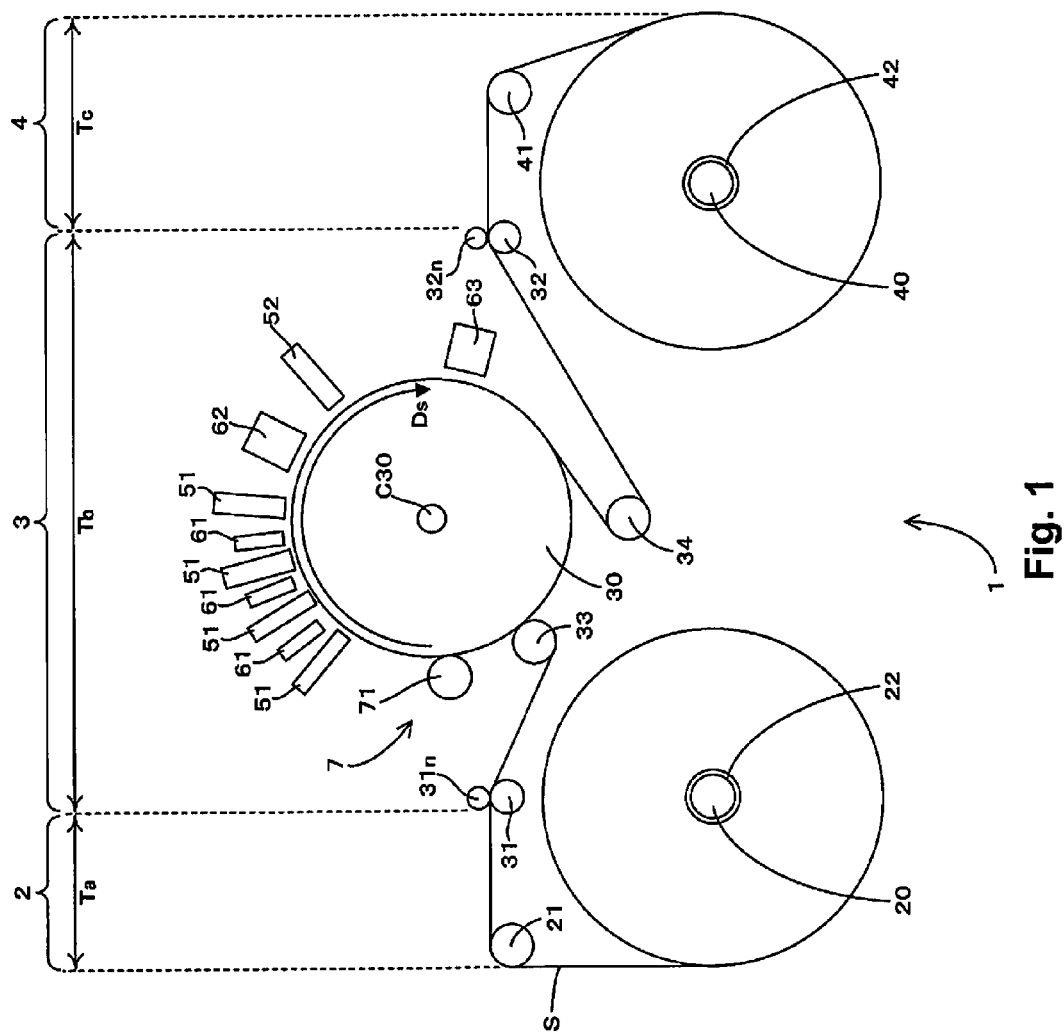
FIG. 1 is a front view schematically illustrating the configuration of a printer to which the present invention has been applied.

FIG. 1 is a front view schematically illustrating the configuration of a printer to which the present invention has been applied. As illustrated in FIG. 1, in a printer 1, a single web S of which both ends have been wound up in the shape of a roll around a feed-out spindle 20 and a take-up spindle 40 is extended in a tensioned state along a conveyance path, and the web S undergoes image recording while also being conveyed in a direction of conveyance Ds going from the feed-out spindle 20 toward the take-up spindle 40. Such webs S are broadly divided into being either paper-based or film-based. As specific examples, paper-based includes high-quality paper, cast paper, art paper, coated paper, and the like, while film-based includes synthetic paper, polyethylene terephthalate (PET) film, polypropylene (PP) film, and the like. As an overview, the printer 1 is provided with: a feed-out part 2 (feed-out region) for feeding the web S out from the feed-out spindle 20; a process part 3 (process region) for recording an image onto the web S having been fed out from the feed-out part 2; and a take-up part 4 (take-up region) for taking the web S, onto which an image was recorded at the process part 3, up into the take-up spindle 40. In the following description, whichever side of the two sides of the web S is the one on which the image is recorded is referred to as the "(front) surface", while the side opposite thereto is referred to as the "reverse surface".

The feed-out part 2 has the feed-out spindle 20, around which an end of the web S has been wound, as well as a driven roller 21 around which the web S having been drawn out from the feed-out spindle 20 is wound. The feed-out spindle 20 supports the end of the web S wound therearound in a state where the front surface of the web S faces outward. When the feed-out spindle 20 is rotated in the clockwise direction in FIG. 1, the web S having been wound around the feed-out spindle 20 is thereby made to pass via the driven roller 21 and fed out to the process part 3. The web S is wound up around the feed-out spindle 20 with a core tube 22 therebetween, the core tube 22 being detachable with respect to the feed-out spindle 20. As such, once the web S on the feed-out spindle 20 has been used up, then a new core tube 22 around which a roll of the web S has been wound can be mounted onto the feed-out spindle 20 to replace the web S of the feed-out spindle 20.

The process part 3 is for performing processes as appropriate and recording an image onto the web S by using a variety of function parts 51, 52, 61, 62, 63 arranged along the outer peripheral surface of a rotating drum 30, while the web S having been fed out from the feed-out part 2 is supported on the rotating drum 30. At this process part 3, a front drive roller 31 and a rear drive roller 32 are provided to both sides of the rotating drum 30; the web S, which is conveyed from the front drive roller 31 to the rear drive roller 32, is supported on the rotating drum 30 and undergoes the recording of an image.

The front drive roller 31 has on the outer peripheral surface a plurality of minute projections formed by thermal spraying, and the web S having been fed out from the feed-out part 2 is wound around from the reverse surface side. When the front drive roller 31 is rotated in the clockwise direction in FIG. 1, the web S having been fed out from the feed-out part 2 is thereby conveyed downstream in the direction of conveyance Ds. Also, a nip roller 31n is provided for the front drive roller 31. This nip roller 31n is in contact with the front surface of the web S in a state of having been urged to the front drive roller 31 side, and nips the web S with the front drive roller 31. This ensures the force of friction between the front drive roller 31 and the web S, and makes it possible for the front drive roller 31 to reliably convey the web S.

The rotating drum 30 is a drum of cylindrical shape having a diameter of, for example, 400 mm, supported so as to be rotatable in both the direction of conveyance Ds and the reverse direction thereof about a rotating shaft C30 thereof, and winds the web S being conveyed from the front drive roller 31 to the rear drive roller 32 up from the reverse surface side. This rotating drum 30 is for supporting the web S from the reverse surface side while also being rotationally driven in the direction of conveyance Ds of the web'S, under the force of friction with the web S. Here, in the process part 3, there are provided driven rollers 33, 34 that loop the web S back at both sides of the part wound about the rotating drum 30. Of these, the driven roller 33 has the front surface of the web S wound around between the front drive roller 31 and the rotating drum 30 and loops the web S back. The driven roller 34, in turn, winds the front surface of the web S around between the rotating drum 30 and the rear drive roller 32 and loops the web S back. In this manner, the web S is looped back on both the upstream and downstream sides of the rotating drum 30 in the direction of conveyance Ds, whereby the length of the section of the web S wound about the rotating drum 30 can be ensured.

The rear drive roller 32 has on the outer peripheral surface a plurality of minute projections formed by thermal spraying, and the web S having been conveyed from the rotating drum 30 via the driven roller 34 is wound therearound from the reverse surface side. When the rear drive roller 32 is rotated in the clockwise direction in FIG. 1, the web S is thereby conveyed toward the take-up part 4. A nip roller 32n is provided for the rear drive roller 32. This nip roller 32n is in contact with the front surface of the web S in a state of having been urged to the rear drive roller 32 side, and nips the web S against the rear drive roller 32. This ensures the force of friction between the rear drive roller 32 and the web S, and makes it possible for the rear drive roller 32 to reliably convey the web S.

In this manner, the web S being conveyed from the front drive roller 31 to the rear drive roller 32 is supported on the outer peripheral surface of the rotating drum 30. Also, at the process part 3, in order to record a color image onto the front surface of the web S being supported on the rotating drum 30, a plurality of recording heads 51 corresponding to mutually different colors are provided. Specifically, four recording heads 51 corresponding to yellow, cyan, magenta, and black are lined up in the stated order of colors in the direction of conveyance Ds. Each of the recording heads 51 faces, spaced apart with a slight clearance, the front surface of the web S having been wound around the rotating drum 30, and discharges ink (coloring ink) of the corresponding color from nozzles in an inkjet format. When each of the recording heads 51 discharges ink onto the web S being conveyed in the direction of conveyance Ds, a color image is thereby formed on the front surface of the web S.

Here, the ink used is a UV (ultraviolet) ink that is cured by being irradiated with ultraviolet rays (light) (i.e., is a photo-curable ink). Therefore, in the process part 3, UV irradiators 61, 62 (irradiation apparatuses) are provided in order to cure the ink and fix the ink to the web S. The execution of this curing of the ink is divided into two stages, which are temporary curing and true curing. A UV irradiator 61 for temporary curing is arranged in between each of the plurality of recording heads 51. Namely, the UV irradiator 61 are intended to irradiate with ultraviolet rays of low irradiation intensity and thereby cure the ink to such an extent that the ink wets and spreads sufficiently slower than when not irradiated with ultraviolet rays (that is, are intended to temporarily cure the ink), and are not intended to truly cure the ink. The UV irradiator 62 for true curing, meanwhile, is provided to the downstream side in the direction of conveyance Ds relative to the plurality of recording heads 51. Namely, the UV irradiator 62 is intended to irradiate with ultraviolet rays of a greater irradiation intensity than the UV irradiators 61, and thereby cure the ink to such an extent that the wetting and spreading of the ink stops (i.e., is intended to truly cure the ink).

In this manner, the coloring inks discharged onto the web S from the recording heads 51 on the upstream side of the direction of conveyance Ds are temporarily cured by the UV irradiators 61 arranged between each of the plurality of recording heads 51. As such, the ink that is discharged onto the web S by one recording head 51 is temporarily cured until reaching the recording head 51 that is adjacent to the one recording head 51 on the downstream side in the direction of conveyance Ds. The occurrence of color mixing, where coloring inks of different colors mix together, is thereby curbed. In this state where color mixing has been curbed, the plurality of recording heads 51 discharge the color inks of mutually different colors and form the color image on the web S. Furthermore, the UV irradiator 62 for true curing is provided further downstream in the direction of conveyance Ds than the plurality of recording heads 51. Therefore, the color image that has been formed by the plurality of recording heads 51 is truly cured by the UV irradiator 62 and fixed onto the web S.

A recording head 52 is also provided to the downstream side in the direction of conveyance Ds relative to the UV irradiator 62. This recording head 52 faces, spaced apart with a slight clearance, the front surface of the web S that is wound up around the rotating drum 30, and discharges a transparent UV ink onto the front surface of the web S in an inkjet format from a nozzle. In other words, the transparent ink is additionally discharged onto the color image formed by the recording heads 51 of the four different colors. This transparent ink is discharged onto the entire surface of the color image, and endows the color image with a glossy or matte texture. A UV irradiator 63 (irradiation apparatus) is also provided to the downstream side in the direction of conveyance Ds relative to the recording head 52. This UV irradiator 63 is intended to irradiate with intense ultraviolet rays and thereby truly cure the transparent ink discharged by the recording head 52. This makes it possible to fix the transparent ink onto the front surface of the web S.

In this manner, at the process part 3, the web S wound around the outer peripheral part of the rotating drum 30 undergoes the discharging and curing of the inks as appropriate, thus forming a color image coated with the transparent ink. The web S on which the color image has been formed is then conveyed toward the take-up part 4 by the rear drive roller 32.

In addition to the take-up spindle 40 around which an end of the web S is wound, the take-up part 4 also has a driven roller 41 around which the web S is wound from the reverse surface side between the take-up spindle 40 and the rear drive roller 32. The take-up spindle 40 supports one end of the web S taken up therearound in a state where the front surface of the web S is facing outward. In other words, when the take-up spindle 40 is rotated in the clockwise direction in FIG. 1, the web S, which has been conveyed from the rear drive roller 32, is taken up around the take-up spindle 40 via the driven roller 41. Here, the web S is taken up around the take-up spindle 40 with a core tube 42 therebetween, the core tube 42 being detachable with respect to the take-up spindle 40. As such, when the web S taken up around the take-up spindle 40 is at capacity, then it becomes possible to remove the web S with the core tube 42.

As stated above, the printer 1 is provided with the recording heads 51, 52 facing the peripheral surface of the rotating drum 30, and executes printing onto the web S by discharging ink from the recording heads 51, 52 onto the web S, which is supported on the peripheral surface of the rotating drum 30. With this printer 1, the clearance (a so-called platen gap) between the rotating drum 30 and each of the recording heads 51, 52 is set so as to be extremely narrow. This makes it possible to curtail the flight time of the ink from being discharged from the recording heads 51, 52 until landing on the web S, and to curb offsetting of the landing positions of the ink due to influences sustained by the ink during flight. With a configuration where the platen gap has been narrowed, however, there is the risk that a foreign matter present on the web S could come into contact with the recording heads 51, 52 and damage the recording heads 51, 52 if such a foreign matter enters between the rotating drum 30 and the recording heads 51, 52. Therefore, the printer 1 is provided with a foreign matter detection unit 7 for detecting a foreign matter present on the web S, on the upstream side of the recording heads 51, 52 in the direction of conveyance Ds. In the present embodiment, a "foreign matter" refers to: paper powder, dust, or dirt; UV ink that has adhered to the printer 1 and then is cured and comes unstuck; wrinkling, creasing, or cracking that has occurred in the web S; or the like.

Figure 2:
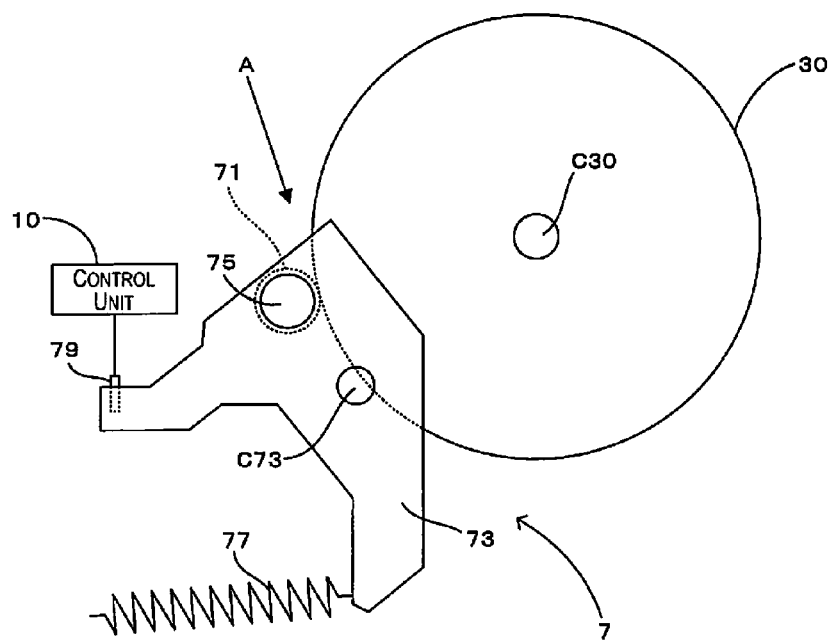
FIG. 2 is a front view schematically illustrating one example of a foreign matter detection unit.
Figure 3:
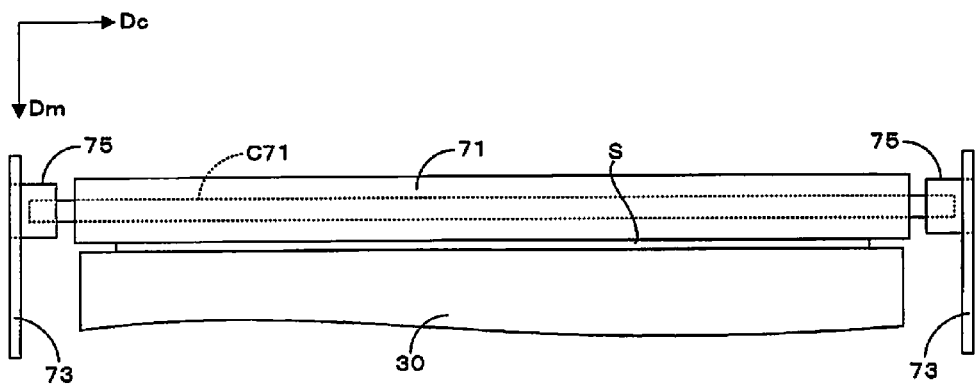
FIG. 3 is a side view schematically illustrating one example of the foreign matter detection unit illustrated in FIG. 2.

FIG. 2 is a front view schematically illustrating one example of a configuration of the foreign matter detection unit. FIG. 3 is a side view schematically illustrating the appearance of the example of the configuration of the foreign matter detection unit illustrated in FIG. 2, as seen from the side (the direction of the arrow A in the drawing). FIGS. 2 and 3 also depict the rotating drum 30, in addition to the foreign matter detection unit 7, while FIG. 2 furthermore depicts a control unit 10 for controlling the overall operation of the printer 1 as a whole. The control unit 10 is a computer constituted of a central processing unit (CPU), a random access memory (RAM), and the like.

The foreign matter detection unit 7 has a movable roller 71 provided in a rotational axis direction Dc parallel to the rotating shaft C30 of the rotating drum 30 (i.e., parallel to the rotational center of the rotating drum 30). As illustrated in FIG. 3, in the rotational axis direction Dc, the movable roller 71 has a width longer than the rotating drum 30, and the two ends of the rotating drum 30 are located on the inside of the two ends of the movable roller 71. The movable roller 71 is arranged so as to face the rotating drum 30, and the web S is nipped between the peripheral surface of the movable roller 71 and the peripheral surface of the rotating drum 30. The movable roller 71 is able to rotate about a rotating shaft C71 thereof, and is rotationally driven in association with the conveyance of the web S under the frictional force against the web S.

In the foreign matter detection unit 7, this movable roller 71 is supported so as to be able to move in a direction Dm of approach towards or withdrawal from the rotating drum 30. The foreign matter detection unit 7 detects a foreign matter on the basis of displacement of the movable roller 71, which is pressed against the foreign matter entering between the movable roller 71 and the rotating drum 30. A more detailed description shall follow.

The foreign matter detection unit 7 is provided with support frames 73 provided to each of two ends of the movable roller 71 in the rotational axis direction Dc, and bearing members 75 attached to each of the support frames 73. The support frames 73 are able to rotate, independently of one another, about the rotating shaft C73 that is parallel to the rotational axis direction Dc of the rotating drum 30. The bearing members 75 are attached to the support frames 73 at positions eccentric to one side from the rotating shaft C73. The two ends of the rotating shaft C71 of the movable roller 71 are each supported by the bearing members 75. As such, the movable roller 71 is able to move in the direction of approach/withdrawal Dm, which is orthogonal to the rotational axis direction Dc, by rotating about the rotating shaft C73 in association with the support frames 73 on both ends. Thus, the movable roller 71 is able to approach the rotating drum 30 or withdraw away from the rotating drum 30 in the direction of approach/withdrawal Dm.

The bearing members 75 supporting the movable roller 71 at both ends are spherical plain bearings. As such, the movable roller 71 can swing about each of the bearing members 75 provided to the two ends, and is able to adopt not only an orientation parallel to the rotational axis direction Dc but also an orientation that is inclined.

The foreign matter detection unit 7 is also provided with a tension spring 77 (elastic member) attached to each of the support frames 73 on the other side (i.e., the opposite side of the bearing member 75 across from the rotating shaft C73) from the rotating shaft C73. In FIG. 2, the right end of the tension spring 77 is attached to the support frame 73, and the left end of the tension spring 77 is attached to a housing (not shown) of the printer 1. In other words, the tension spring 77 urges the support frame 73 in the clockwise direction in FIG. 2. This causes the movable roller 71 to be urged in a direction approaching the rotating drum 30 in the direction of approach/withdrawal Dm, and pressed against the rotating drum 30 with the web S in between.

With this foreign matter detection unit 7, when a foreign matter present on the web S enters between the movable roller 71 and the rotating drum 30, the movable roller 71 is pushed by the foreign matter against the elastic force of the tension spring 77, and displaced in a direction away from the rotating drum 30 in the direction of approach/withdrawal Dm. Therefore, the foreign matter detection unit 7 is provided with an optical sensor 79 for detecting the displacement of the movable roller 71 in order to detect a foreign matter. This optical sensor 79 is arranged so as to face an edge of at least one of the two support frames 73, and outputs a signal corresponding to the position of the edge of the support frame(s) 73. In other words, the optical sensor 79 detects displacement of the movable roller 71 on the basis of displacement of the edge of the support frame(s) 73. A foreign matter on the web S can thus be detected on the basis of the output of this optical sensor 79.

Specifically, the control unit 10 detects whether or not there is a foreign matter on the web S by analyzing the output of the optical sensor 79. When the presence of a foreign matter is detected, the control unit 10 stops the rotation of the front drive roller 31 and the rear drive roller 32, and stops the conveyance of the web S. The control unit 10 also notifies a user that a foreign matter has been detected. Specific methods for notifying the user include a display on a display screen, emitting a buzzer sound, flashing a warning light, or a variety of other methods.

As described above, in the present embodiment, the movable roller 71 is rotatably supported on the bearing member 75 in a state of being inclinable relative to the rotational axis direction Dc, which is the center of rotation of the rotating drum 30. As such, in a case such as where the peripheral surface of the rotating drum 30 has been deformed, the movable roller 71 can be inclined in conformity with such deformation. As a result, any clearance between the movable roller 71 and the web S supported by the rotating drum 30 is curbed, and it becomes possible to improve the accuracy of detection of a foreign matter present on the web S.

In addition, the foreign matter detection unit 7 has the tension spring 77 for urging the support frames 73 toward the rotating drum 30. With such a configuration, the urging force of the tension spring 77 makes it possible for the movable roller 71, which is inclined in conformity with the deformation of the peripheral surface of the rotating drum 30, to be pressed toward the rotating drum 30. As a result, any clearance between the movable roller 71 and the web S supported by the rotating drum 30 can be more reliably curbed.

Figure 4:
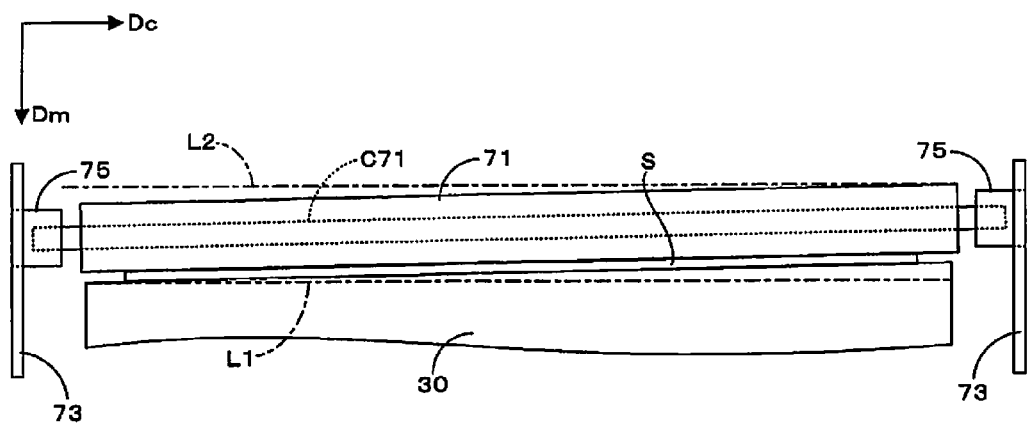
FIG. 4 is a drawing schematically illustrating an example of operation of a movable roller when a peripheral surface of a rotating drum is inclined.

FIG. 4 is a drawing schematically illustrating one example of the operation of the movable roller n a case where the peripheral surface of the rotating drum is inclined. In the illustrated example, the peripheral surface of the rotating drum 30 is inclined relative to a virtual straight line L1 parallel to the rotational axis direction Dc. In contrast, the movable roller 71 is urged toward the peripheral surface of the rotating drum 30 in a state of being able to swing about each of the bearing members 75 on both ends. Therefore, the movable roller 71 is inclined relative to a virtual straight line L2 parallel to the rotational axis direction Dc, so as to follow the inclination of the peripheral surface of the rotating drum 30. As a result, any clearance between the movable roller 71 and the web S supported by the rotating drum 30 is curbed, and it becomes possible to improve the accuracy of detection of a foreign matter present on the web S.

As described above, it is particularly suitable to apply the present invention to the printer 1 with which the UV ink is cured by being irradiated with light from the UV irradiators 61, 62, 63. Namely, with this printer 1, the reaction heat of the UV ink associated with the curing is likely to cause the rotating drum 30 to undergo thermal deformation. Therefore, applying the present invention makes it possible to curb any clearance between the movable roller 71 and the web S supported by the rotating drum 30, even in spite of thermal deformation of the rotating drum 30, and possible to improve the accuracy of detection of a foreign matter present on the web S.

The configuration of the present invention is also useful in instances where there is not so much thermal deformation from the rotating drum 30. Namely, if the rotating drum 30 is formed in a state where the peripheral surface of the rotating drum 30 is inclined in the rotational axis direction Dc, then the position of the peripheral surface of the rotating drum 30 ends up vibrating in association with the rotation of the rotating drum 30. As a result, there is the result of a large clearance occurring between the movable roller 71 and the web S supported by the rotating drum 30. In contrast, according to the configuration of the present invention, it becomes possible to curb such a clearance.

In a case where there is very slight deformation of the peripheral surface of the rotating drum 30, then there may conceivably also be instances where there is little effect on the accuracy of detection of a foreign matter. The configuration of the present invention is believed to be useful even in such instances. Namely, a clearance occurs between the movable roller 71 and the web S supported by the rotating drum 30 if the peripheral surface of the rotating drum 30 is deformed, even if the deformation of the peripheral surface of the rotating drum 30 is very slight. As a result, if the load required for conveyance of the web S by the front drive roller 31 or the rear drive roller 32 fluctuates and the conveyance of the web S becomes unstable, then a problem could arise in that the ink discharged from the recording heads 51, 52 lands on the web S at offset positions, and proper printing cannot be performed. In contrast, according to the configuration of the present invention, the occurrence of such a clearance can be curbed. As such, fluctuations in the load required to convey the web S can be curbed, the web S can be conveyed stably, and printing can be executed properly.

Thus, in the present embodiment, the printer 1 corresponds to one example of a "liquid discharge apparatus" of the present invention; the rotating drum 30 corresponds to one example of a "support member" of the present invention; the recording heads 51, 52 correspond to one example of a "head" of the present invention; the front drive roller 31 and the rear drive roller 32 cooperate to function as one example of a "conveyance part" of the present invention; the foreign matter detection unit 7 corresponds to one example of a "foreign matter detection unit" of the present invention; the movable roller 71 corresponds to one example of a "movable roller" of the present invention; the bearing members 75 correspond to one example of a "rotational support member" of the present invention; the support frames 73 correspond to one example of a "retention member" of the present invention; the tension spring 77 corresponds to one example of an "urging member" of the present invention; the optical sensor 79 corresponds to one example of a "sensor" of the present invention; the UV irradiators 61, 62, 63 correspond to one example of a "light irradiation part" of the present invention; and the web S corresponds to one example of a "medium" of the present invention.

The present invention is not to be limited to the embodiment described above; rather, a variety of different modifications can be added to what has been described above, provided that there is no departure from the spirit of the present invention. For example, in the embodiment described above, the bearing members 75 were spherical plain bearings, but the bearing members may also be resin bearings with which the recording heads 51 are supported by a resin. In short, the bearing members 75 need only be able to support the movable roller 71 so as to allow inclination relative to the rotational axis direction Dc of the rotating drum 30.

A variety of modifications can also be made to the specific configuration of the movable roller 71. Therefore, for example, the hardness of the peripheral surface where the movable roller 71 is in contact with the web S may be configured so as to be 80 degrees or more. With such a configuration, it is possible to curb deformation of the peripheral surface of the movable roller 71 associated with contact with a foreign matter. As a result, the movable roller 71 can be precisely displaced in association with the passing of a foreign matter between the movable roller 71 and the rotating drum 30.

The peripheral surface at which the movable roller 71 is in contact with the web S may be constituted of a rubber roller formed of rubber, or a tetrafluoroethylene/perfluoroalkyl vinyl ether copolymer (PFA) roller formed of PFA. With such a configuration, in a case where a foreign matter has stuck to the web S, the surface of the web S can be protected from damage such as denting caused by the foreign matter in association with the passing of the foreign matter through between the movable roller 71 and the rotating drum 30.

The configuration of the support frames 73 for retaining the movable roller 71 and the configuration for urging the movable roller 71 toward the rotating drum 30 can also be modified as appropriate.

A variety of different contents are also conceivable regarding the analysis of the output of the optical sensor 79 executed by the control unit 10 in order to detect a foreign matter. For example, in a configuration where the movable roller 71 is displaced in association with deformation of the rotating drum 30, as described above, it would be appropriate to be able to distinguish between whether the displacement of the movable roller 71 is caused by a foreign matter or caused by deformation of the rotating drum 30. Therefore, a threshold value may be provided between (for example, in the middle of) an expected value (about 50 μm) for the amount of displacement of the movable roller 71 due to deformation of the peripheral surface of the rotating drum 30, and an expected value (350 to 800 μm) for the amount of displacement of the movable roller 71 caused by a foreign matter. In other words, the configuration of the control unit 10 need only be such that it is determined that a foreign matter has been detected in an instance where the movable roller 71 has had displacement exceeding this threshold value. The threshold value here should be a suitable value that has been ascertained in advance by testing.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A liquid discharge apparatus, comprising:
   a support member configured to support a medium while rotating;
   a head facing the support member and configured to discharge a liquid onto the medium supported by the support member;
   a conveyance part configured to convey the medium between the support member and the head; and
   a foreign matter detection unit configured to detect a foreign matter heading toward between the support member and the head, in association with a conveyance of the medium by the conveyance part,
   the foreign matter detection unit having
      a movable roller facing the support member on an upstream side of the head in a direction of conveyance of the medium being conveyed by the conveyance part, the movable roller being configured to nip the medium between the support member and the movable roller,
      a rotational support member rotatably supporting the movable roller so as to allow inclination of the movable roller relative to a rotational axis direction, which is a center of rotation of the support member, and
      a retention member movably retaining the rotational support member in a direction going toward the support member.

2. The liquid discharge apparatus as set forth in claim 1, wherein
   the foreign matter detection unit further has an urging member configured to urge the retention member toward the support member.

3. The liquid discharge apparatus as set forth in claim 1, wherein
   the rotational support member is a spherical plain bearing.

4. The liquid discharge apparatus as set forth in claim 1, wherein
   the rotational support member supports the movable roller by using a resin.

5. The liquid discharge apparatus as set forth in claim 1, wherein
   the support member is a rotating drum.

6. The liquid discharge apparatus as set forth in claim 1, wherein
   the movable roller has a peripheral surface at which the movable roller is in contact with the medium, and a hardness of the peripheral surface of the movable roller is 80 degrees or higher.

7. The liquid discharge apparatus as set forth in claim 1, wherein
   the foreign matter detection unit has a sensor configured to detect displacement of the movable roller relative to the support member.

8. The liquid discharge apparatus as set forth in claim 7, wherein
   the sensor is configured to detect the displacement of the movable roller based on displacement of the retention member.

9. The liquid discharge apparatus as set forth in claim 1, further comprising a light irradiation part configured to irradiate the liquid discharged onto the medium from the head with light, the liquid being cured while being heated while irradiated with the light from the light irradiation part.

* * * * *